United States Patent
Spenciner et al.

(10) Patent No.: US 9,089,322 B2
(45) Date of Patent: Jul. 28, 2015

(54) SUTURE PASSER WITH EXPELLING MECHANISM

(71) Applicant: DePuy Mitek, LLC, Raynham, MA (US)

(72) Inventors: David B. Spenciner, North Attleboro, MA (US); Justin M. Piccirillo, Uxbridge, MA (US); Jeffery Tolonen, Franklin, MA (US)

(73) Assignee: DePuy Mitek, LLC, Raynham, MA (US)

( * ) Notice: Subject to any disclaimer, the term of this patent is extended or adjusted under 35 U.S.C. 154(b) by 104 days.

(21) Appl. No.: 13/731,912

(22) Filed: Dec. 31, 2012

(65) Prior Publication Data

US 2014/0188137 A1  Jul. 3, 2014

(51) Int. Cl.
*A61B 17/04* (2006.01)
*A61B 17/06* (2006.01)

(52) U.S. Cl.
CPC ... *A61B 17/0483* (2013.01); *A61B 2017/06009* (2013.01); *A61B 2017/06042* (2013.01)

(58) Field of Classification Search
CPC ............... A61B 17/04; A61B 17/0469; A61B 17/0482; A61B 17/0483; A61B 17/0491; A61B 17/062; A61B 2017/0498; A61B 2017/00663; A61B 2017/06057; A61B 2017/0474
See application file for complete search history.

(56) References Cited

U.S. PATENT DOCUMENTS

| | | | |
|---|---|---|---|
| 4,235,238 A | 11/1980 | Ogiu et al. | |
| 5,499,991 A * | 3/1996 | Garman et al. | 606/148 |
| 5,817,112 A * | 10/1998 | Christoudias | 606/148 |
| 7,585,305 B2 | 9/2009 | Dreyfuss | |
| 2004/0127915 A1 | 7/2004 | Fleenor et al. | |
| 2009/0082787 A1 | 3/2009 | Pang | |
| 2010/0042117 A1 | 2/2010 | Kim et al. | |
| 2012/0271323 A1 | 10/2012 | Fan et al. | |

* cited by examiner

*Primary Examiner* — Tuan V Nguyen (57) ABSTRACT

A suture passing mechanism is disclosed having an elongated delivery member and a suture capture fitting at a distal end of the delivery member. The suture capture fitting includes a recess for receiving a length of suture. The recess is bounded by a proximal wall and a lateral opening leads therein. An expeller at the recess is adapted to expel suture out of the recess through the lateral opening.

15 Claims, 7 Drawing Sheets

SUTURE PASSER WITH EXPELLING MECHANISM

BACKGROUND

The present invention relates to suture passers and graspers and more particularly to such instruments and methods for their use wherein provision is made to eject the suture therefrom.

Within the field of medical surgery, there are times when a suture needs to be passed through soft tissue, but direct access to the tissue is not possible (e.g. during arthroscopy). Generally, this passage of suture is performed either anterograde or retrograde. In anterograde passing an instrument called a suture passer grasps a strand of suture and is forcibly driven through the soft tissue. Then, the suture is disengaged from the passer and the passer removed from the tissue. Retrograde passing involves driving an empty passer through the soft tissue and then manipulating it such that it captures a length of suture already inside the body. The passer is then removed from the soft tissue and pulls the suture through with it. In both of these cases, one major drawback of the suture passer is that it can be quite difficult to disengage the suture from the jaws of the passer. This is particularly true for the anterograde technique and is mainly due to the fact that the passer jaws open into a fairly large cavity. The surgeon must manipulate the tip of the passer to cause the suture to move sufficiently out of the open jaws that closing the open jaws will no longer cause the suture to become re-trapped by the passer. This process of manipulation can lead to trauma to the surrounding soft tissue up to and including the suture passer ripping through the soft tissue, foiling the repair intent of the suturing and forcing the surgeon to pursue alternate courses of repair of patient treatment. The cavity frequently also is provided with a lip or other structure to assist in the process of capturing the suture, but such features can add difficulty when the surgeon later attempts to expel the suture.

SUMMARY OF THE INVENTION

A suture passing mechanism according to the present invention comprises an elongated delivery member having a suture capture fitting at a distal end thereof. The suture capture fitting comprises a recess for receiving a length of suture. The recess has a proximal wall and a lateral opening leading therein. An expeller at the recess is adapted to expel suture out of the recess through the lateral opening.

Preferably, the expeller comprises a surface movable across the recess toward the lateral opening whereby to push the suture out of the lateral opening. In one embodiment, the expeller comprises a line affixed adjacent the lateral opening. It is received within the recess and spaced apart from the opening in a first position and adjacent the lateral opening in a second position. In one aspect of the invention, the line is biased into the first position and tension applied to the line moves it into the second position. Alternatively, axial compression applied to the line moves it into the second position. It can also be moved into the second position by removing tension applied to the line or removing compression applied to the line.

A method according to the present invention provides for passing suture through tissue. The method comprises the steps of: capturing a suture into a recess in a suture capture fitting on a distal end of an elongated delivery member; passing the suture through the tissue via the delivery member; and expelling the suture out of the recess through a lateral opening into the recess via an expeller in the recess.

In one aspect of the invention, a surface on the expeller is moved across the recess toward the lateral opening to push the suture out of the lateral opening. The expeller can comprise a line affixed adjacent the lateral opening and received within the recess so that it is spaced apart from the opening in a first position and adjacent the lateral opening in a second position such that the line is moved from the first position to the second position to expel the suture out of the lateral opening. The method can further comprise the step of biasing the line into the first position. The method can further comprise the step of applying, removing, increasing, or decreasing tension or compression to the line to move it into the second position.

DETAILED DESCRIPTION

Figure 1:
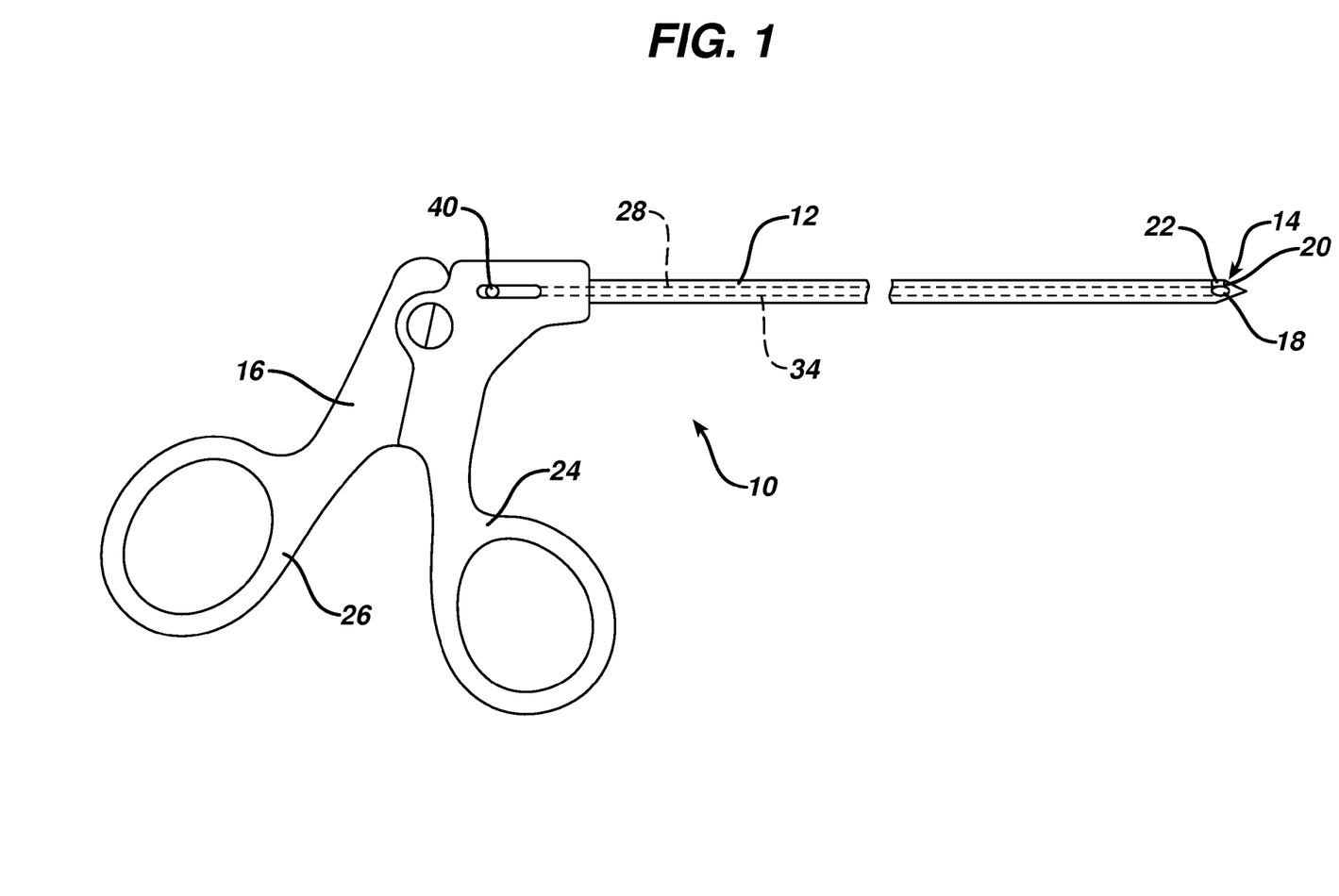
FIG. 1 is a side elevation view of a suture passer according to the present invention.

FIG. 1 illustrates a suture grasper 10 according to the present invention. It comprises in gross an elongated shaft 12 having a distal grasping mechanism 14 and a proximal scissor handle 16. The grasping mechanism 14 comprises a suture capture recess 18 having a lateral opening 20 and an articulating jaw 22. The handle 16 comprises a fixed arm 24 and an articulating arm 26 connected to the articulating jaw 22 via a rod or wire 28 whereby articulation of the arm 26 translates into articulation of the jaw 22.

Figure 2A:
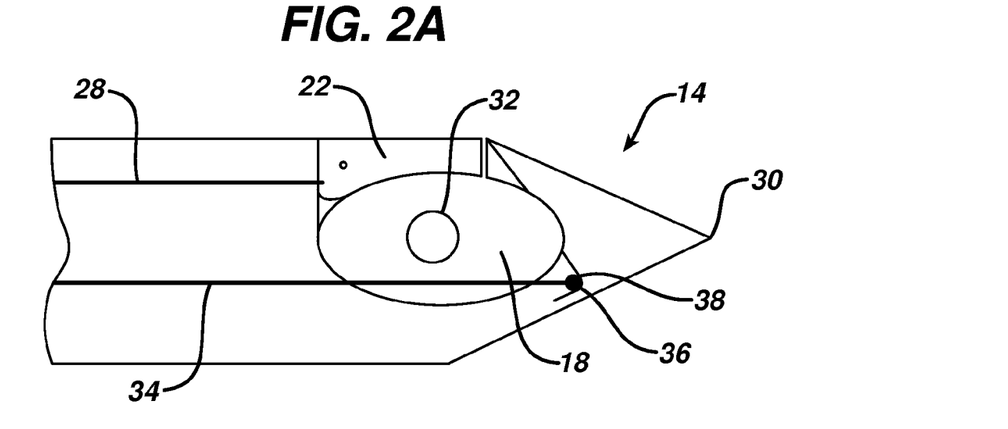
FIGS. 2A to 2C are side elevation views of a suture grasping mechanism with an expelling feature at a distal end of the suture passer of FIG. 1.
Figure 2B:
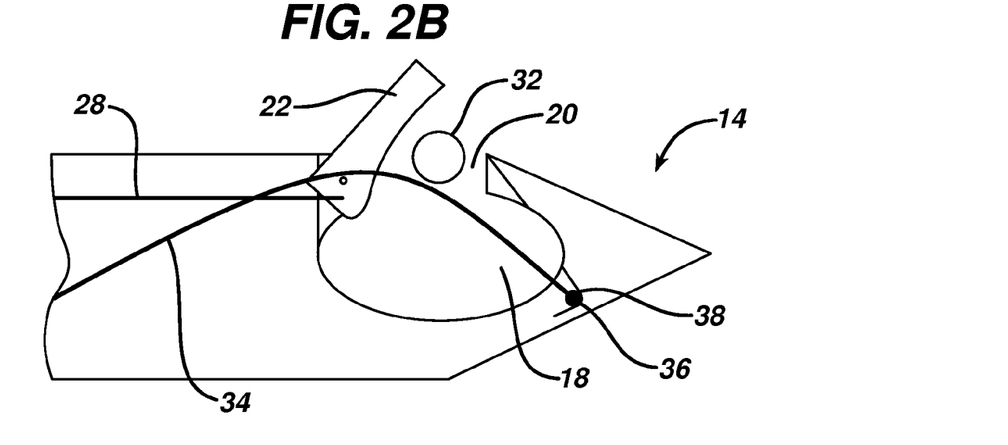
Figure 2C:
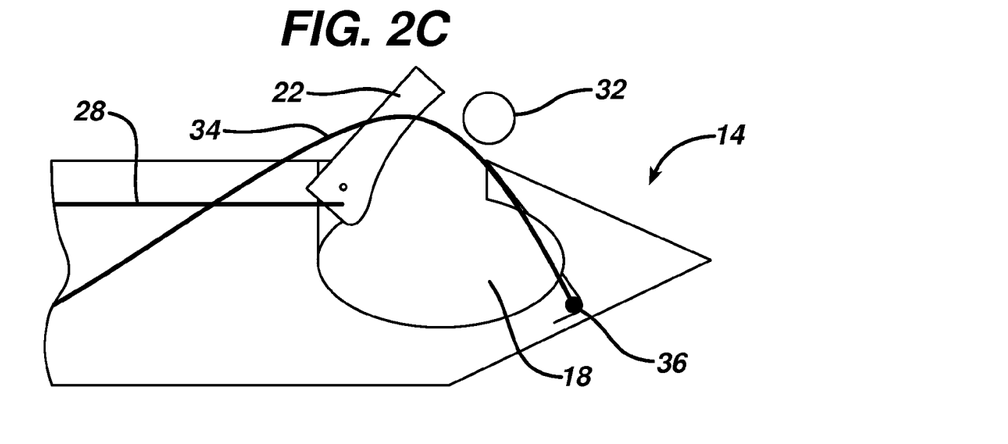

Turning also now to FIGS. 2A to 2C, the shaft 12 optionally terminates with a sharp distal tip 30 for passing a portion of the shaft 12 and the grasping mechanism 14 through tissue (not shown) to grab or release a suture 32. The suture 32 is captured in the recess 18 (FIG. 2A). It can then be manipulated in a procedure such as being pulled back through the tissue. To release the suture 32 the jaw 22 is opened (FIG. 2B).

To assist in releasing the suture 32 from the recess 18 an expeller wire 34 is bowed outwardly toward the opening 20 to push the suture 32 out of the opening 20 (FIG. 2C). The expeller wire 34 is preferably a flexible but stiff wire that will bow when put into compression. It could be formed from a superelastic material such as NITINOL, but the invention need not be limited thereto. Other suitable materials include nylon, stainless steel, polyesters and elastomeric materials. The wire 34 preferably terminates in a ball 36 received within a cup 38 within the recess 18. The cup 38 can be open or partially enclosed so as to retain the ball 36 therein while allowing rotation. Preferably, the cup 38 opens toward the opening 20 to encourage the wire 34 to rotate and bow in such direction when placed into compression. The wire 34 extends along the shaft 12 and terminates at the handle 16 in a button 40 or other mechanism to allow a user to apply compressive force thereto. Alternatively, the wire 34 could also be connected to the articulating arm 26 of the handle 16 so that a single action by a user would open the jaw 22 and activate the expeller wire 34 to expel the suture 32 from the recess 18.

Other configurations for the wire 34 are possible. It can be pre-bent in the direction of the opening 20 to encourage it to bow in that direction under compression. This feature can be incorporated into the wire 34 along with the ball 36 and cup 38 or with some other attachment of the wire 34, such as the wire simply being welded to the wall of the recess 18. Rather than terminate in a ball 36 the wire 34 could terminate in a cylinder (not shown) received in a transverse bore adjacent the recess 18 with the wire 34 movable in a closed ended slot open toward the opening 20 thereby promoting rotation of the cylinder and wire toward the opening upon compression of the wire 34. The compression applied is relative to any force on the wire 34 when it is in the position within the recess shown in FIG. 2A. For instance, if an open cup 38 is employed the wire might be biased toward the cup 38 to hold it in place and then when additional compressive force is applied the wire 34 will bow outwardly toward the opening 20.

Figure 3A:
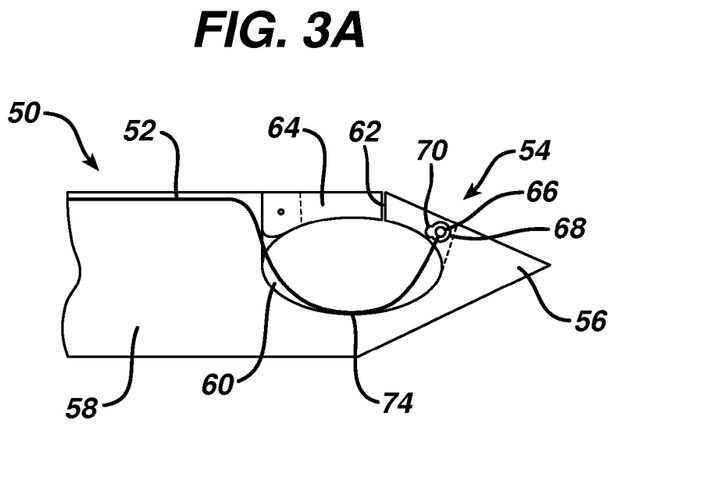
FIGS. 3A to 3C are side elevation views of a further suture grasping mechanism according to the present invention with an alternative expelling feature.
Figure 3B:
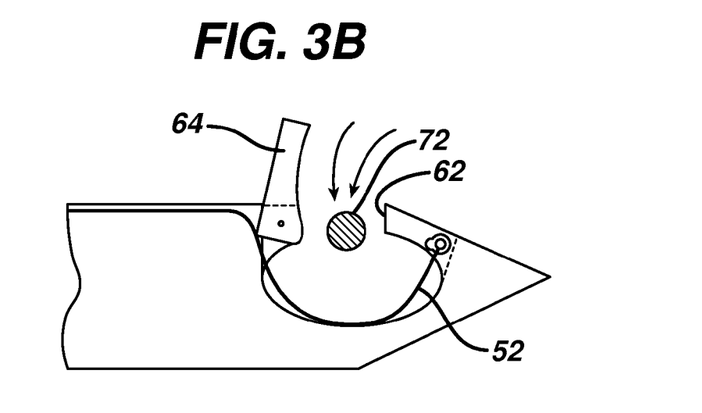
Figure 3C:
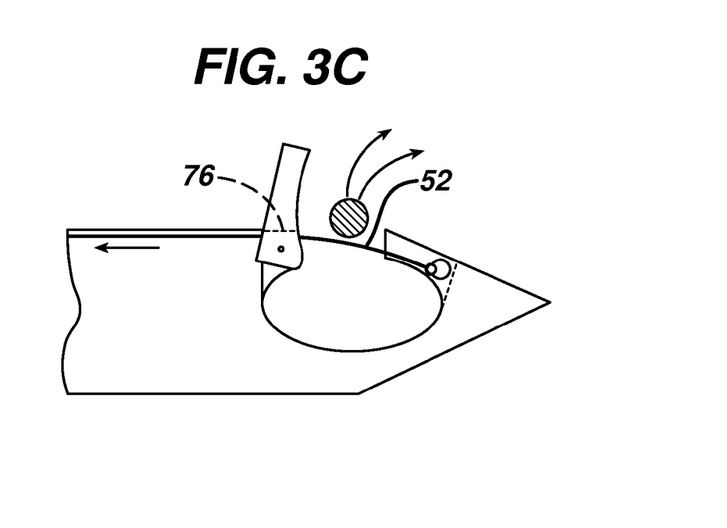

Turning also now to FIGS. 3A to 3C an alternative embodiment of a suture grasper 50 is shown wherein tension force applied to an expeller wire 52 initiates the expelling action. The grasper 50 comprises a grasping mechanism 54 on a distal end 56 of a shaft 58 and having a recess 60 with a lateral opening 62 enclosed by an articulating jaw 64 across the opening 62 (FIG. 3A). The wire 52 terminates in a distal, transverse cylinder 66 which rotates in a transverse bore 68 adjacent to the recess 60. A closed end slot 70 is open toward the opening 62 to encourage the cylinder 66 and wire 52 to rotate toward the opening when tension is applied to the wire 52. The wire 52 is pre-bent to normally bow outwardly away from the opening 62 leaving the recess 60 open for receipt of a suture 72 (FIG. 3B). A groove 74 in the wall of the recess 60 adjacent the jaw 64 allows the wire 52 to follow a path into the recess 60 without obstructing the recess 60. When tension force is applied to the wire 52 it straightens and moves toward the opening 62 to eject the suture 72 from the recess 60 (FIG. 3C). A slot 76 in the jaw 64 allows the wire 52 to take this configuration unimpeded by the jaw 64. The term "tension" is used here relative to the state of the wire 52 as shown in FIGS. 3A and 3B in which the wire could be put into less compression to encourage it to bow outwardly away from the opening 62 than it was in FIG. 3A.

Figure 4:
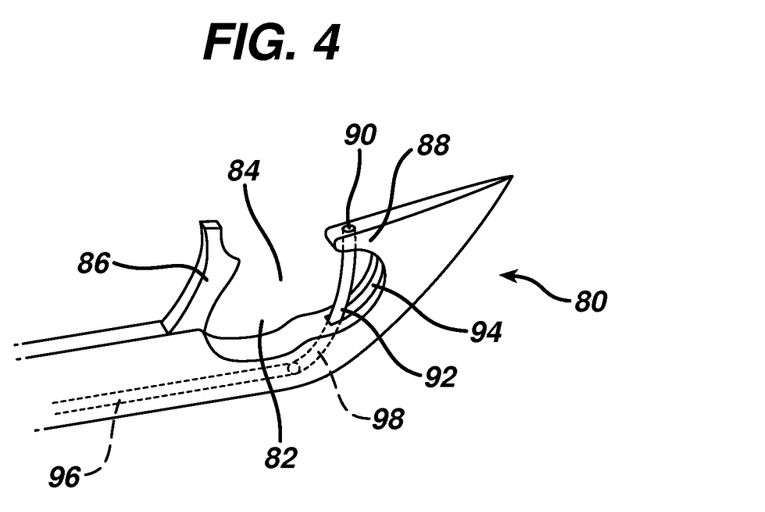
FIG. 4 is a side elevation view of a further suture grasping mechanism according to the present invention with an alternative expelling feature.

FIG. 4 illustrates a further embodiment of a suture grasper 80 having a recess 82 with a lateral opening 84 and an articulating jaw 86 enclosing the opening 84. The recess 82 is C-shaped and forms a distal lip 88. This feature aids in capturing suture (not shown in FIG. 4) into the recess 82 but can impair release of suture from the recess 82. A first end 90 of an expeller rod 92 attaches to the lip 88 adjacent the opening 84 and is received within a groove 94 in the wall of the recess 82 which extends partially therealong from the lip 88. An actuating rod or wire 96 attaches to a second end 98 of the rod 92 to control its articulation from position received within the groove 94 leaving the recess 82 fully open to a position as shown in FIG. 4 where it is moved partially toward the opening 84 to bridge the overhang of the lip 88 and to thereby reduce or eliminate the ability of the lip 88 to entrap suture in the recess 82. It does not fully expel the suture but allows it to more easily move out of the recess 82 unimpeded by the lip 88. The rod 92 can be formed of a resilient material to encourage it to bow into the groove 94. Alternatively, a wire as in the previous embodiments could be substituted for the rod 92 and be oriented similarly to operate to diminish the effect, when desired, of the lip 88. Another option would be to form an effective lip with the wire such as with a living hinge point.

Figure 5:
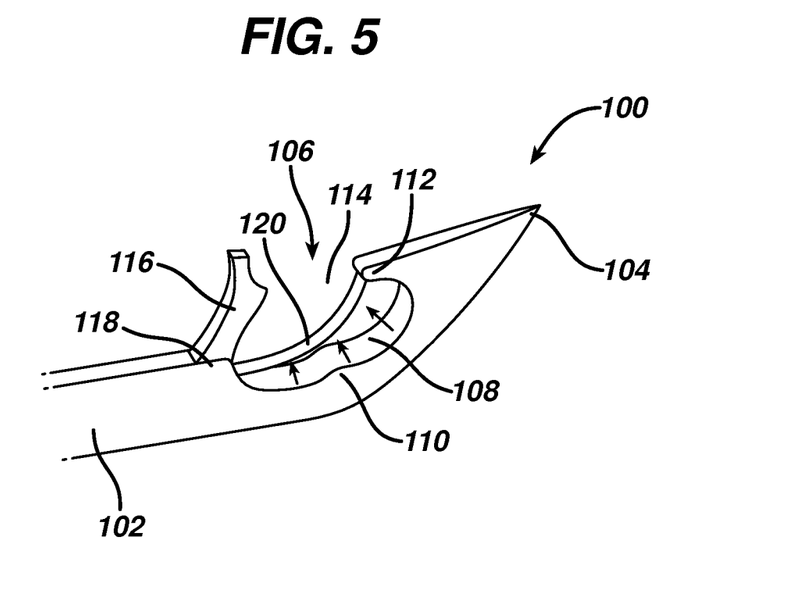
FIG. 5 is a side elevation view of an alternative suture grasping mechanism for a suture passer according to the present invention.

FIG. 5 illustrates a further embodiment of a suture passer 100 according to the present invention. It comprises an elongated shaft 102 terminating in a sharp distal tip 104 for penetrating tissue (not shown) with a grasping mechanism 106 immediately proximal thereto. The penetrating mechanism 106 comprises a recess 108 formed of a wall 110 and having a distal overhanging lip 112. It further comprises a lateral opening 114 which can be spanned by an articulating jaw 116 pivotable about an axis 118. An ejector arm 120 connects to and articulates in unison with the jaw 116. When the jaw 116 is in a closed position, spanning and closing the opening 114, the ejector arm 120 is received deeply within the recess 108. A groove (not shown) can be provided in the wall 110 to receive the ejector arm 120 to minimize or eliminate its obstruction of the recess 108 in this position. When the jaw 116 is pivoted outwardly away from the opening 114 the ejector arm 120 pivots outwardly away from the wall 110 forming the recess 108, preferably connecting to the lip 112. If suture (not shown in FIG. 5) is received within the recess 108 it will now be possible to slip the suture out of the recess 108 without it getting caught up on the lip 112. The jaw 116 and ejector arm 120 form a V-shaped opening in this position suitable for suture capture. To enhance capture employing the lip 112 to snag a suture a user can place the jaw 116 and ejector arm 120 into an intermediate position in which the opening 114 is not closed by the jaw 116 and the lip 112 is not completely obstructed by the ejector arm 120. Alternatively, the jaw 116 and ejector arm 120 can be adapted for independent articulation.

Figure 6A:
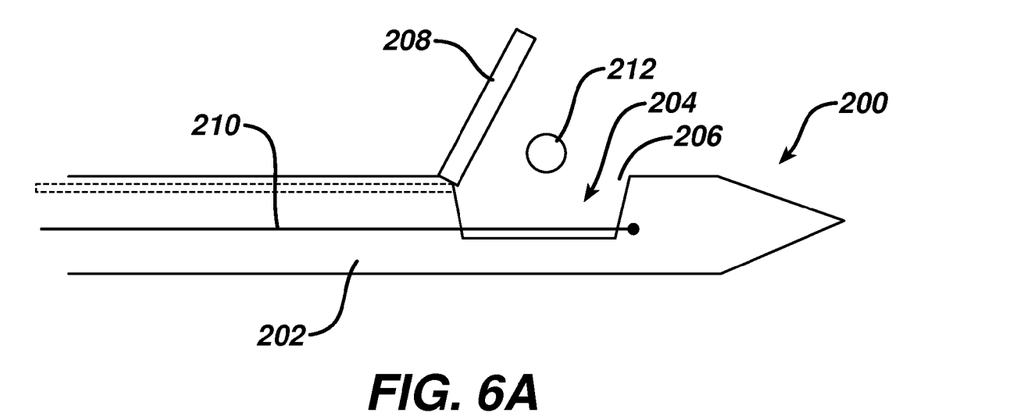
FIGS. 6A to 6C are side elevation views of a further suture grasping mechanism according to the present invention.
Figure 6B:
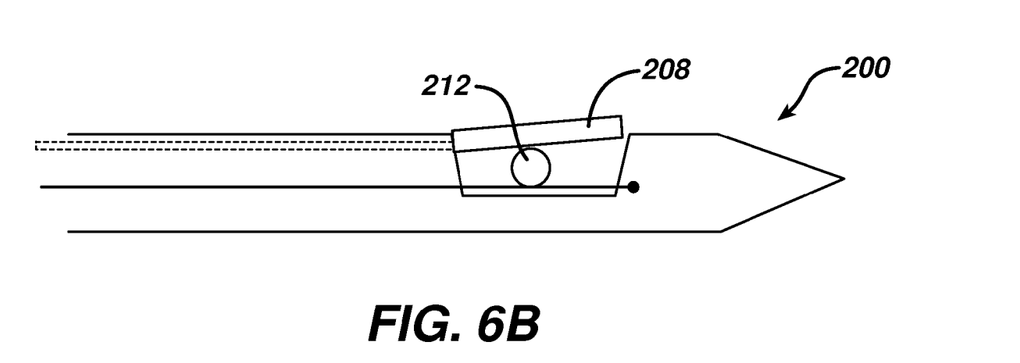
Figure 6C:
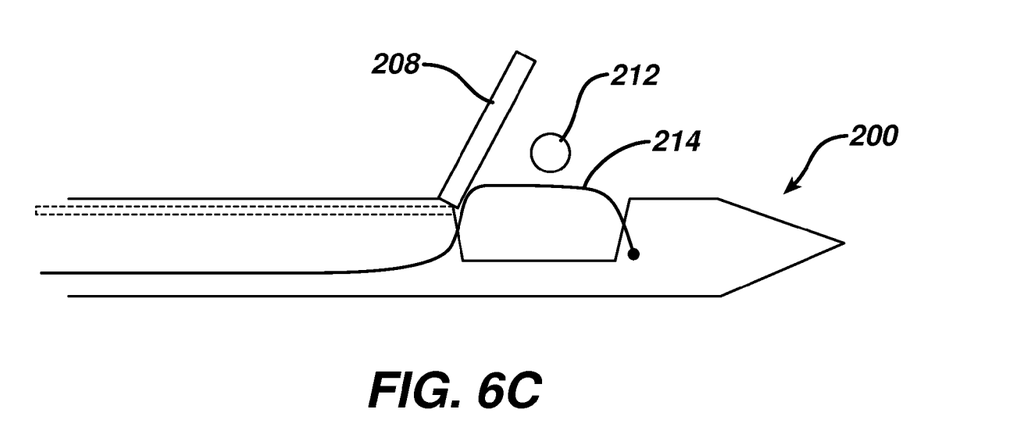

FIGS. 6A to 6C illustrate a further embodiment of a suture grasper 200 according to the present invention. It comprises a shaft 202 having a suture capture recess 204 having a lateral opening 206 and an articulating jaw 208. An expeller wire 210 at the recess 204 is placed in tension during capture of a suture 212 to hold the wire 210 out of the path of the suture 212 into the recess 204 (FIG. 6A). The jaw 208 is closed to hold the suture 212 in the recess 204 and preferably the expeller wire 210 is maintained in tension during this time (FIG. 6B). When it is desired to expel the suture 212 the articulating jaw 208 is opened and tension is released on the expeller wire 210 (FIG. 6C). The expeller wire 210 has a preformed curvature 214 which when the tension is released expels the suture 212 from the recess 204. Preferably the expeller wire is formed of a superelastic material.

Figure 7A:
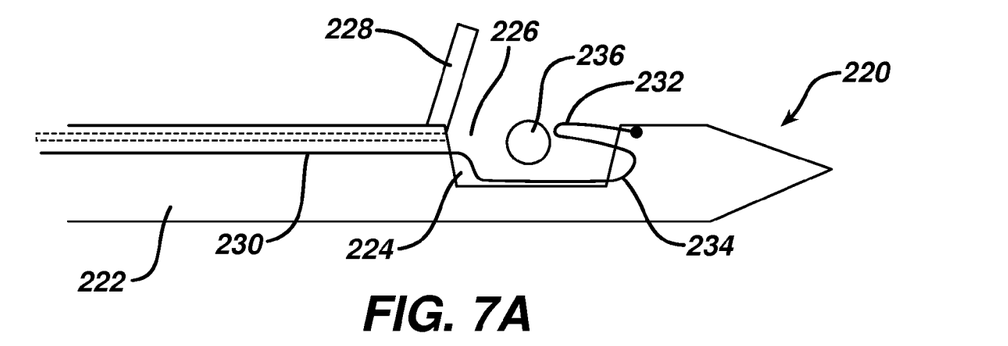
FIGS. 7A to 7C are side elevation views of a further suture grasping mechanism according to the present invention.
Figure 7B:
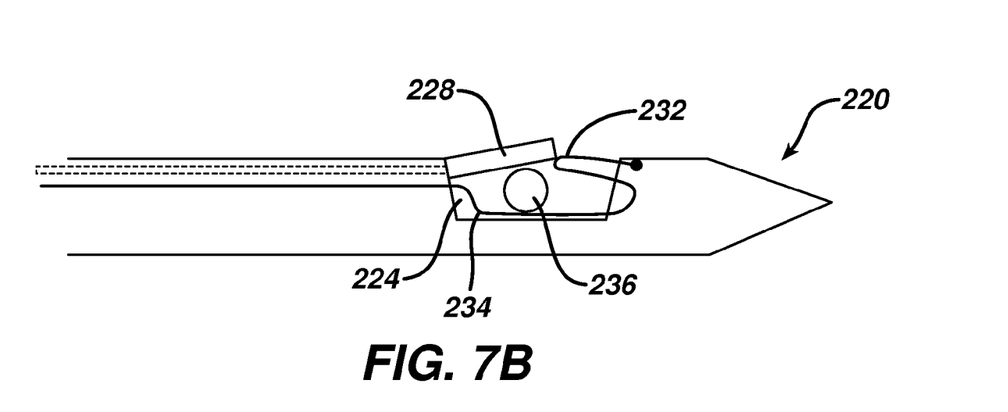
Figure 7C:
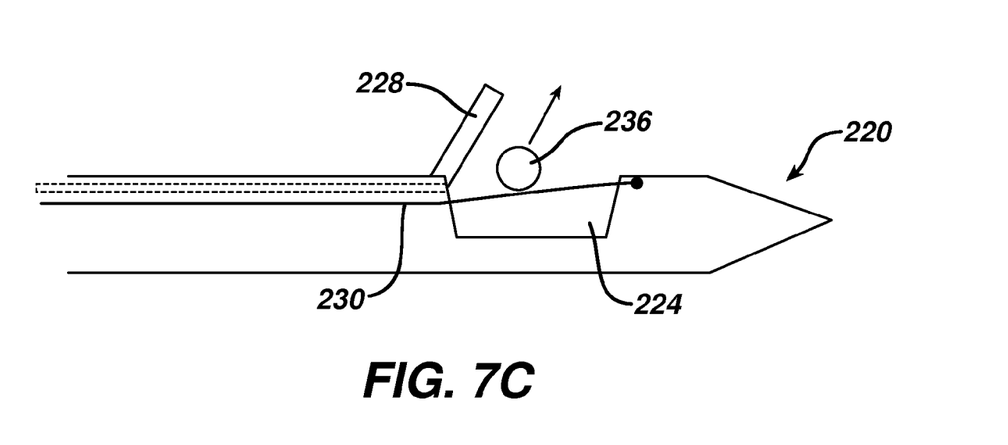

FIGS. 7A to 7C illustrate a further embodiment of a suture grasper 220 according to the present invention. It comprises a shaft 222 having a suture capture recess 224 having a lateral opening 226 and an articulating jaw 228. An expeller wire 230 is affixed adjacent the opening 226 and when under no or reduced tension has a preformed shaped which forms a lip 232 at the recess 224 and also a curvature 234 into the recess 224. Suture 236 is captured into the recess 224 with the assistance of the lip 232 (FIG. 7A) and then retained therein by closure of the jaw 228 (FIG. 7B). To eject the suture 236 the jaw 228 is opened and tension applied to the expeller wire 230 to straighten it thereby eliminating, or substantially reducing, the curvature 234 and the lip 232 thus pushing the suture 236 out of the recess 224.

Figure 8A:
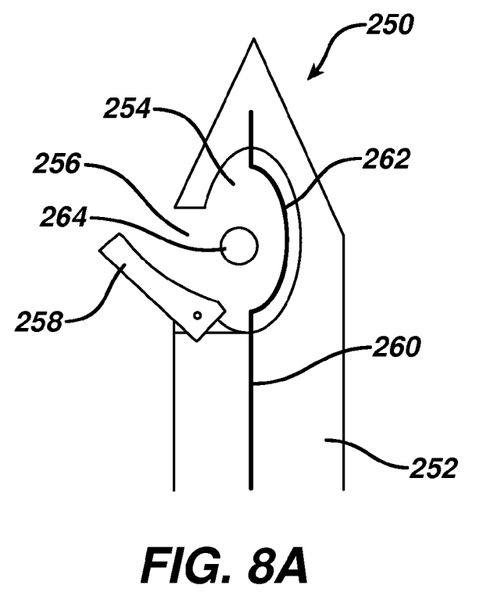
FIGS. 8A to 8C are side elevation views of a further suture grasping mechanism according to the present invention.
Figure 8B:
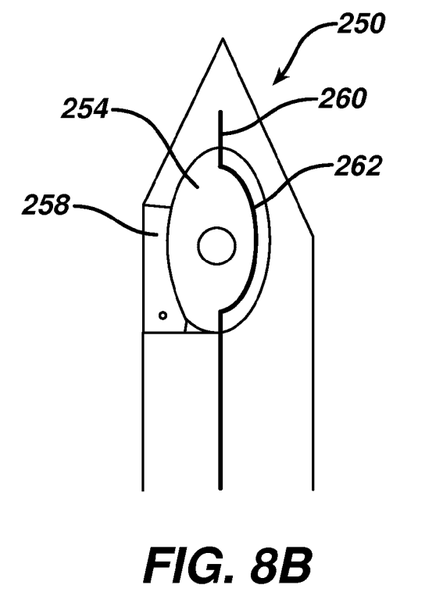
Figure 8C:
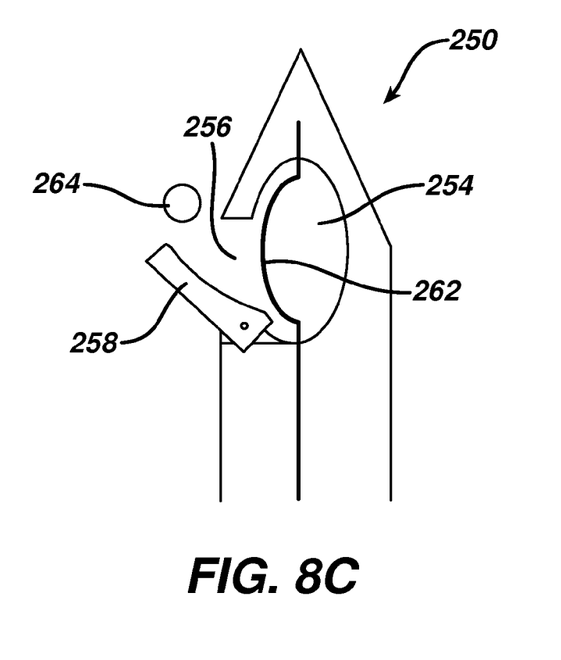

FIGS. 8A to 8C illustrate a further embodiment of a suture grasper 250 according to the present invention. It comprises a shaft 252 having a suture capture recess 254 having a lateral opening 256 and an articulating jaw 258. An ejector 260 having a curvature 262 is positioned within the recess 254.

Preferably it comprises a wire. The ejector 260 is rotatable such that during capture of a suture 264 (FIG. 8A) the curvature 262 is away from the opening 256 to allow entry of the suture 264 into the recess 254. The jaw 258 is then closed to hold the suture 264 in the recess 254. To eject the suture 264 the jaw 258 is opened and the ejector is rotated to swing the curvature 262 toward the opening 256 thereby pushing the suture 264 out of the recess 254.

While the invention has been particularly described in connection with specific embodiments thereof, it is to be understood that this is by way of illustration and not of limitation, and that the scope of the appended claims should be construed as broadly as the prior art will permit.

What is claimed is:

1. A suture passing mechanism comprising
    an elongated delivery member; and
    a suture capture fitting at a distal end of the delivery member, the suture capture fitting comprising a recess for receiving a length of suture, the recess having a proximal wall and a lateral opening leading therein and an expeller at the recess adapted to expel suture out of the recess through the lateral opening;
    the expeller comprising a line affixed adjacent the lateral opening and received within the recess spaced apart from the lateral opening in a first position and adjacent the lateral opening in a second position whereby the line is moved from the first position to the second position to push the suture out of the lateral opening; and
    a jaw at the lateral opening movable from a closed position in which the jaw blocks the lateral opening to an open position in which the jaw is away from the lateral opening.

2. The suture passing mechanism according to claim 1 wherein the expeller comprises a surface movable across the recess toward the lateral opening whereby to push the suture out of the lateral opening.

3. The suture passing mechanism according to claim 1 wherein the line is biased into the first position.

4. The suture passing mechanism according to claim 3 wherein tension applied to the line moves it into the second position.

5. The suture passing mechanism according to claim 3 wherein axial compression applied to the line moves it into the second position.

6. The suture passing mechanism according to claim 3 wherein removing tension applied to the line moves it into the second position.

7. The suture passing mechanism according to claim 3 wherein removing compression applied to the line moves it into the second position.

8. The suture passing mechanism according to claim 1 and further comprising a suture received within the recess between the line and the lateral opening.

9. A method for passing suture through tissue comprises the steps of:
    capturing a suture into a recess in a suture capture fitting on a distal end of an elongated delivery member;
    passing the suture through the tissue via the delivery member; and
    expelling the suture out of the recess through a lateral opening into the recess via an expeller in the recess; and
    wherein the expeller comprises a line affixed adjacent the lateral opening and received within the recess spaced apart from the lateral opening in a first position and adjacent the lateral opening in a second position and wherein the line is moved from the first position to the second position so that a surface on the expeller is moved across the recess toward the lateral opening to push the suture out of the lateral opening.

10. The method according to claim 9 and further comprising the step of biasing the line into the first position.

11. The method according to claim 10 and further comprising the step of applying tension to the line to move it into the second position.

12. The method according to claim 10 and further comprising the step of applying compression to the line to move it into the second position.

13. The method according to claim 10 and further comprising the step of removing tension from the line to move it into the second position.

14. The method according to claim 10 and further comprising the step of removing compression from the line to move it into the second position.

15. The method according to claim 9 and further comprising prior to the step of expelling the suture performing the step of moving a jaw on the capture fitting from a closed position in which the jaw blocks the lateral opening to an open position in which the jaw is away from the lateral opening.

* * * * *